United States Patent [19]
Lipsky et al.

[11] Patent Number: 5,676,924
[45] Date of Patent: Oct. 14, 1997

[54] IN VIVO ASSAY TO DETERMINE CANCER TREATMENT EFFECTIVENESS

[75] Inventors: Milton H. Lipsky, West Greenich, R.I.; Justiniano F. Bagtas, St. Petersburg, Fla.; Edwin N. Forman, Providence, R.I.

[73] Assignee: Rhode Island Hospital, Providence, R.I.

[21] Appl. No.: 169,312

[22] Filed: Dec. 17, 1993

Related U.S. Application Data

[63] Continuation of Ser. No. 769,968, Oct. 2, 1991, abandoned.

[51] Int. Cl.$^6$ .............................. A61K 49/00; C12N 5/00
[52] U.S. Cl. .......................... 424/9.2; 424/9.1; 435/240; 435/242
[58] Field of Search .............................. 424/9, 93.7, 9.2, 424/9.1; 435/240, 242

[56] References Cited

U.S. PATENT DOCUMENTS

| | | |
|---|---|---|
| 4,324,683 | 4/1982 | Lim et al. . |
| 4,352,883 | 10/1982 | Lim . |
| 4,353,888 | 10/1982 | Seftom . |
| 4,391,909 | 7/1983 | Lin . |
| 4,409,331 | 10/1983 | Lim et al. . |
| 4,495,288 | 1/1985 | Lim et al. . |
| 4,892,538 | 1/1990 | Aebischer et al. . |

FOREIGN PATENT DOCUMENTS

| | | |
|---|---|---|
| 0218400 | 4/1987 | European Pat. Off. . |
| 218400 | 4/1987 | European Pat. Off. . |
| 207 3007 | 9/1971 | France . |
| WO 89/04655 | 6/1989 | WIPO . |
| WO 91/15245 | 10/1991 | WIPO . |

OTHER PUBLICATIONS

Shockley et al., "Penetration of Tumor Tissue by Antibodies and Other Immunoproteins", *Annals New York Academy of Science*, pp. 367–382.

Selby et al., "Use of the Agar Diffusion Chamber for the Exposure of Human Tumor Cells in Drugs", *Cancer Research* 42:4758–4762 (1982).

Allen et al., "Novel Method of Evaluating Antiviral Drugs Against Human Cytomegalovirus in Mice", *Antimicrobial Agents and Chemotherapy* 36(1):206–208 (1992).

Chen et al., "Microencapsulated of Tumor Cells and Assay for Selecting Anticancer Drugs", *Proc. Natl. Sci. Counc.* B. ROC 12(4):252–260 (1988).

Hwang, "A New In Vivo Assay of the Reactions of Microencapsulated Human tumor Cells to Chemotherapeutic Drugs", *Chin. Med. J. (Taipei)* 51:166–175 (1993).

Li et al., "A New In Vivo Anti-Viral Assay Using Microencapsulated Infected Cell Cultures", *Antiviral Research* 10:179–192 (1988).

McMahon et al., "Feasibility of Cellular Microencapsulation Technology for Evaluation of Anti–Human Immunodeficiency Virus Drugs in Vivo", Reports 82(22):1761–1765 (1990).

Chu et al., "Differential Characteristics of Two Newly Established Human Breast Carcinoma Cell Lines", Cancer Res. 45:1357–1366 (Mar. 1985).

Chu et al., "Potentiation of 5–Fluoro–2–'–Deoxyuridine Antineoplastic Activity by the Uridine". . . Cancer Res 44:1852–1856 (May 1984).

Tibbetts et al., "Chemotherapy of Cell–Line–Derived Human Colon Carcinoma in Mice Immunosuppressed With Antithymocyte Serum," Cancer (Phila.) 40:2651–2659, 1977.

Chu et al., "9–Deazaadenosine"–A New Potent Antitumor Agent, Biochem. Pharmacol. 33:1229–1234 (1984).

Gorelik, E., et al., "Microencapsulated Tumor Assay: New Short–Term Assay for in Vivo Evaluation of the Effects of Anticancer Drugs on Human Tumor Cell Lines", *Cancer Research*, vol. 47, pp. 5739–5747 (1987).

Phillips, R. M., Bibby, M.C., Double, J.A., "A Critical Appraisal of the Predictive Value of in Vitro Chemosensitivity Assays", *Journal of the National Cancer Institute*, vol. 82, No. 18, pp. 1457–1468 (1990).

Hall, T. C., ed., "Prediction of response to cancer chemotherapy", *Progress in Clinical Biologic Research*, vol. 276, pp. 1–225 (188).

Sun, Anthony M., "Encapsulated Verses Modified Endocrine Cells for Organ Replacement", Editorial, vol. XXXIII *Trans Am Soc. Artif Inter Organs*, pp. 787–790, 1987.

Aebischer, Patrick, et al., "Long–Term Cross–Species Brain Transplantation of a Polymer–Encapsulated Dopamine–Secreting Cell Line", *Experimental Neurology*, vol., 111, pp. 269–275, 1991.

Aebischer, Patrick, et al., "A Bioartificial Parathyroid", vol. XXXII *Trans Am Soc Artif Intern Organs*, pp. 134–137, 1986.

Lamberton, Preston, et al., "Use of Semipermeable Polyurethane Hollow Fibers for Pituitary Organ Culture", *In Vitro Cellular & Development Biology*, vol. 24, No. 6, pp. 500–504, Jun. 1988.

Sullivan, Susan, J., et al., "Biohybrid Artificial Pancreas: Long–Term Implantation Studies in Diabetic Pancreatectomized Dogs", *Science*, vol. 252, pp. 718–721, Oct. 15, 1990.

Aebischer, P., et al., "Coextrusion of Acrylic Copolymer Macrocapsules Loaded with Dopamine Secreting Cells as Potential Neural Implants", Articial Organ Laboratory, Brown University, The 16th Meeting of the Society Biomaterials, May 20–23, 1990.

(List continued on next page.)

*Primary Examiner*—Deborah Crouch
*Attorney, Agent, or Firm*—Morgan, Lewis and Bockius, LLP

[57] ABSTRACT

A method of determining the effectiveness of a cancer treatment by sealing tumor cells in segments of semipermeable membrane hollow fibers, implanting the sealed fiber segments in a mammal, treating the mammal with a cancer treatment, and evaluating the effect of the cancer treatment on the cells in the hollow fiber segments.

23 Claims, 6 Drawing Sheets

OTHER PUBLICATIONS

Von Hoff, Daniel, D. et al., "Improved Plating Efficiencies for Human Tumors Cloned in Capillary Tubes *verses* Petri Dishes", *Cancer. Research*, vol. 46, pp. 4012–4017, Aug. 1986.

McMahon et al (1990) J. Natl. Cancer Inst. 82, 1761–1762.
Lehnert et al (1990) Rad. Res. 124, 208–215. Yang et al. (1990) Radiother. Oncol. 19, 49–56.
Mori et al (1990) Dis. Col. Rect. 33, 590–593.
Rafstad et al. (1990) Int. J. Rad. Biol. 57, 1113–1122.

IN VIVO ASSAY TO DETERMINE CANCER TREATMENT EFFECTIVENESS

This is a continuation of application Ser. No. 07/769,968, filed Oct. 2, 1991, now abandoned.

BACKGROUND OF THE INVENTION

The invention relates to determining the effectiveness of a cancer treatment in vivo.

Cancer treatments have included chemotherapy (i.e., drugs), radiation therapy, immunotoxins (i.e., antibodies specific for a particular tumor cell attached to a toxin), and biological modifiers. As some treatments work better than others for different kinds of tumors and in different patients (e.g., some chemotherapy agents work better than others for different tumors), it is desirable to have an idea of the particular treatment having the best likelihood of being effective before administering to a specific patient. Various in vitro assays have been reported for determining the effectiveness of chemotherapy agents. While they may be useful in predicting drug resistance, they have been poor predictors of tumor drug sensitivity, often producing false positive results, as reported in Phillips, R. M., Bibby, M. C., Double, J. A., "A Critical Appraisal of the Predictive Value of In Vitro Chemosensitivity Assays", *Journal of the National Cancer Institute*, Vol. 82, No. 18, pp. 1457–1468 (1990) and Hall, T. C., ed., "Prediction of response to cancer chemotherapy", *Progress in Clinical Biologic Research*, Vol. 276, pp. 1–225 (1988).

Gorelik, E., et al., "Microencapsulated Tumor Assay: New Short-Term Assay for in Vivo Evaluation of the Effects of Anticancer Drugs on Human Tumor Cell Lines", *Cancer Research*, Vol. 47, pp. 5739–5747 (1987) describes injecting microcapsules filled with human tumor cells into nude mice and administering drugs to evaluate their effectiveness in vivo.

SUMMARY OF THE INVENTION

The invention features, in general, determining the effectiveness of a cancer treatment by sealing tumor cells (especially those obtained from a particular patient) in segments of semipermeable membrane hollow fibers, implanting the sealed fibers in a mammal, treating the mammal with a particular cancer treatment (e.g., chemotherapy agent, immunotoxin, radiation or biological modifier) and evaluating the effect of the cancer treatment on the cells in the hollow fibers. The fibers have a molecular weight cutoff that permits passage of nutrients but blocks passage of agents of the mammal's immune system, providing reliable immunoprotection for the cells in the fiber and advantageously making it possible to implant malignant human tumor cells in an immunocompetent animal. The implanted fibers permit good tumor cell proliferation and permit the use of tissue explants.

In preferred embodiments the cells can be cells in suspension or cells in the form of a tissue explant. The fibers are preferably implanted intraperitoneally, though they could be implanted in other locations, e.g., subcutaneously. The fibers preferably are polysulfone fibers designed to have a pore size that excludes agents capable of mediating tissue rejection (molecular weight pore size cutoff of 30,000 to 50,000 Daltons). The pore size can be varied to allow entry of immunotoxins while preventing animal cell rejection. The mammal preferably is an immunocompetent rat.

The presently preferred cancer therapy to be evaluated is chemotherapy. Administration of drug(s) can follow standard or innovative treatment protocols, and drug metabolism and bioavailability resemble those of the patient. Thus drugs that require in vivo metabolism for activation (e.g., cyclophosphamide and ifosfamide) and drugs that act on actively proliferating cells (methotrexate) can be tested. Different chemotherapy agents can be administered simultaneously to different mammals receiving fibers with cells from the same tumor in order to compare the results of use of different chemotherapy agents or combinations of agents. The assay can provide quick results, e.g., within 72 hours, under conditions that simulate actual use in a patient. In addition to testing the effectiveness of various established chemotherapy agents for a particular patient's tumor cells, the method can be used to evaluate potential new drugs for their effectiveness under in vivo conditions. The method could also be used in studies of multiple drug resistance. Besides chemotherapy, the method can also be used to evaluate other cancer treatments, e.g., immunotoxins, radiation treatment, and biological modulators.

In another aspect the invention features a mammal implanted with one or more semipermeable membrane hollow fibers containing tumor cells therein. The mammals maintain the cells in vivo and are administered with a cancer treatment being evaluated. The mammal-implanted fibers provide an ideal environment to maintain the cells while waiting for treatment. This environment permits shipping of the mammal loaded with fibers to remote laboratories for evaluation of cancer treatment there. In addition, the mammal might have different fibers that contain different cancer cells (as from different patients), permitting a single mammal to be used to evaluate a variety of possible uses for new treatments. A large number of mammals might be implanted with fibers containing different types of cancer cells at a central location, and these mammals could then be shipped to various remote laboratories that could then evaluate their own individual treatments without the need to do tumor cell preparation, fiber sealing, and implanting there.

Other advantages and features of the invention will be apparent from the following description of the preferred embodiment thereof and from the claims.

DESCRIPTION OF THE PREFERRED EMBODIMENT

The drawings will be described first.

Drawings FIG. 1 is a diagram of an implantable diffusion chamber according to the invention.

OPERATION

The cancer treatment assay according to the invention includes the steps of obtaining tumor cells, sealing tumor cells in segments of semipermeable membrane hollow fibers, implanting the sealed fibers in a mammal, treating the mammal with the cancer treatment, and evaluating the effect of the cancer treatment on the cells in the hollow fibers. These steps will be different depending upon the source of the cells, whether a tissue explant or dissociated cells are employed, and the type of treatment. In all methods, the same preferred hollow fiber segments, fiber end sealing technique, and method of implanting can be employed.

If the tumor cells are obtained from a tumor surgically removed from a patient, a tissue explant can be employed, in which case there would be a qualitative evaluation of treatment effectiveness, e.g., by study of morphology. Alternatively, the cells can be disassociated from each other, and cell counts can be employed to have a quantitative evaluation of treatment effectiveness.

Figure 1:
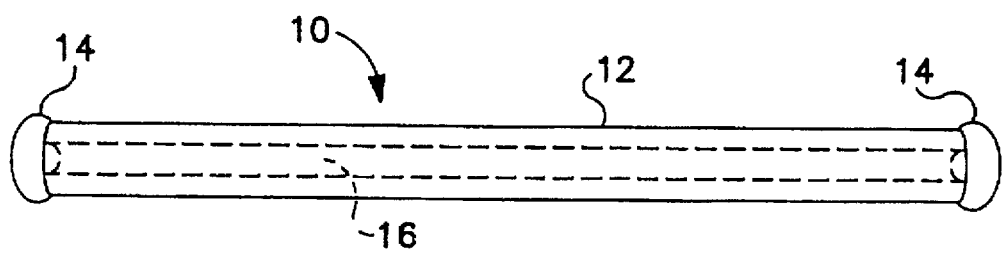
Figure 2:
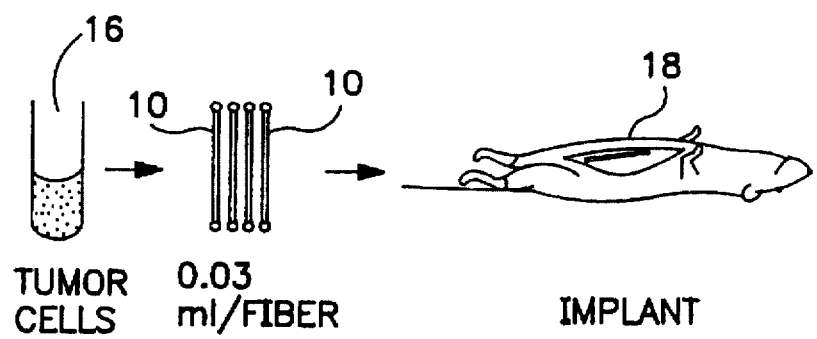
FIG. 2 is a diagram illustrating implantation in the in vivo assay according to the invention.
Figure 3:
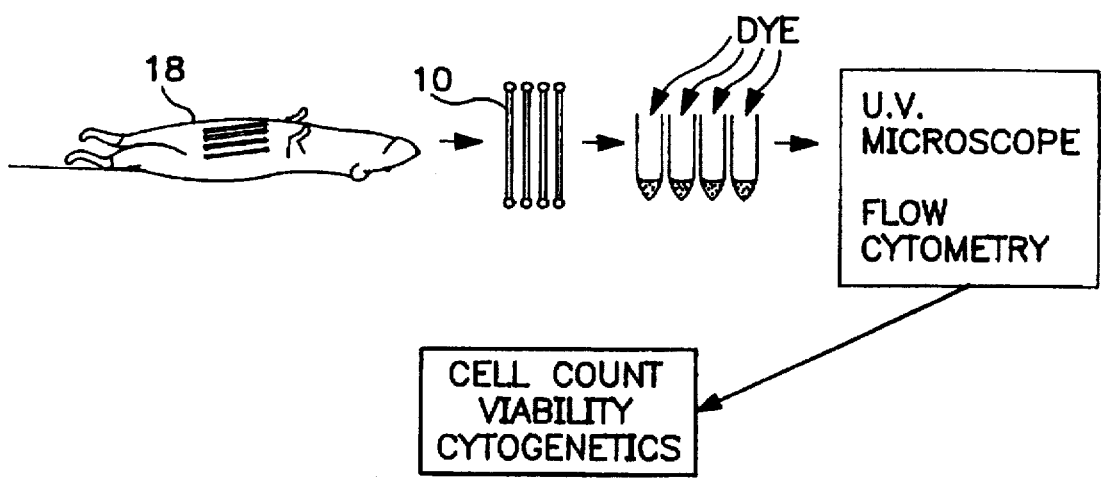
FIG. 3 is a diagram illustrating harvesting and treatment evaluation in the in vivo assay according to the invention.

If tissue explants are to be employed, the tumor material removed from the patient is placed in RPMI 1640 medium, and then cut (in the medium) with a scalpel to provide minced fragments about 0.25 to 0.5 mm in size. The tumor material in the suspension 16 (FIGS. 1 and 2) is then loaded into hollow fiber segments 12 by inserting the tip of a blunt needle syringe into one end of a fiber segment 12 (FIG. 1), placing the other end into the liquid containing the minced fragments of tumor material, and withdrawing a known volume of the medium-suspended fragments. The ends of the fiber segments 12 are then clamped shut with hemostats. The presently preferred fiber segments 12 are 30 mm lengths of semipermeable polysulfone ultrafiltration fibers having an internal diameter of 1.5 mm and a molecular weight cutoff of 30,000 Daltons (available from A. G. Technology, Wexford St., Needham, Mass.). The fiber segments are soaked in alcohol and washed with saline to sterilize them and make them hydrophilic. If disassociated cells are to be employed, a cell suspension of tumor cells is obtained from the tumorous material removed from the patient using well known disassociation techniques, e.g., as described in Hixson, D. C., "Characterization of a Family of Glycoproteins Associated with the Bile Canalicular Membrane of Normal Hepatocytes but not Expressed by Two Transplantable Rat Hapatocellural Carcinomas", *Cancer Research*, Vol. 43, pp. 3874–3884 (August 1983) or in the Hall reference cited earlier. The cells are in RPMI 1640 medium and are counted and diluted to provide a known cell concentration, e.g., between 100K and 6M cells/ml. A pipette is used to measure standard volumes (e.g., between 20–30 microliters) of cell suspension 16 and deliver the volumes into the fiber segments 12.

The ends of fiber segments (whether containing the tissue explants or suspension) are sealed using resin that is heated on a hot plate and applied with a Q-tip type applicator to the ends of the segments, which are then dipped into saline to cool and harden to provide end seal caps 14. A preferred resin is available from 3M under the "hot melt gue" 3738AE trade designation. The resin advantageously provides a reliable seal that avoids leakage into or out of the sealed fiber segment 10.

The loaded fiber segments 10 are implanted in mammals. Typically a plurality (e.g., three or four) are implanted in a single mammal, and a plurality of mammals (e.g., four to six) are implanted with identical fiber segment samples to provide a control. The presently preferred mammals are rats 18, though mice and other mammals could be used. An advantage of the invention is that immunocompetent animals can be employed. Intraperitoneal implants are presently preferred, though subcutaneous implants and implants in other locations can be used. When doing a intraperitoneal implant, a small midline skin incision is made; the linear albea is cut; the peritoneum is lifted, and the fibers are inserted. The peritoneum is then sutured, and skin clips are used to close the skin. When doing a subcutaneous implant, the fiber segments are placed just under the skin.

The rats with the implants are then subjected to the cancer treatment or treatments being evaluated, and rats are sacrificed periodically, e.g., once every 24 hours, and the fiber segments from the sacrificed rats are examined to determine the effectiveness of the treatment. Typically about half of the rats are treated, and the other half are used to provide control rats to be sacrificed each time that a treated rat is sacrificed. When evaluating chemotherapy treatment, the chemotherapy agent could be administered 48 hours after implant, and a rat would be sacrificed at that time (as a control), and a treated rat and a control rat would be sacrificed 24 hours and possibly also 48 hours after implant.

When the implanted cells are disassociated cells in suspension, the cells in the fiber are counted using techniques well known in the art. E.g., a flow cytometer can be used to automatically count the viable cells, or a hemocytometer can be used to count the viable cells that are a different color than dead cells after staining. Radiolabelled thymidine uptake can also be monitored.

When the implanted cells are tissue explants, tissue morphology is examined microscopically to qualitatively evaluate the effectiveness of the treatment. Vital stains which differentiate live tumor cells from dead cells will quantify cytoxic effect.

Preferably a plurality of different chemotherapy agents are evaluated simultaneously, permitting the treating physician to select the treatment most likely to be the most effective with the patient.

The invention also has application in evaluating potential new drugs in vivo on a quick, cost-efficient basis without using humans. In this case the tumor cells employed could be a commercially available cell line such as the human T-cell leukemia cell line (MOLT-4) or cells available from other sources. The cells could also be any of the wide variety of cells available from the National Disease Research Interchange, 2401 Walnut St., Suite 408, Philadelphia, Pa.

The mammal-implanted fibers provide an ideal environment to maintain the cells while waiting for treatment. The environment permits shipping of mammals loaded with fibers to remote laboratories for evaluation of different cancer treatments there. A mammal can have different fibers that contain different cancer cells and are marked with an identification, permitting a single mammal to be used to evaluate a variety of possible uses for new treatments. A large number of mammals can be implanted with fibers containing different types of cancer cells at a central location, and these mammals could then be shipped to various remote laboratories that could then evaluate their own individual treatments without the need to do tumor cell preparation, fiber sealing, and implanting at the remote locations.

The invention provides a rapid, resource efficient and cost effective method for evaluating old or new potential anticancer agents in a system providing immunoprotection and physiologic exposure to the treatment. The use of fibers is particularly advantageous for providing a reliable molecular weight cutoff, a large volume in the diffusion chamber, and ease of harvesting.

OTHER EMBODIMENTS

Other embodiments of the invention are within the scope of the claims. For example, besides chemotherapy, the method can also be used to evaluate other cancer treatments, e.g., immunotoxins, radiation treatment, and biological modifiers such as interferon and retinoic acid. Also, besides polysulfone fibers, other semipermeable membrane hollow fibers, e.g., acrylic copolymer membranes, can be used, including membranes with molecular weight cutoffs greater than 30,000 Daltons, so long as they block passage of agents of the host mammal's immune system.

Features and advantages of this invention are further illustrated by the following examples, but the particular materials and amounts thereof recited in these examples, as well as other conditions and details, should not be construed to limit this invention.

EXAMPLE 1

Figure 4:
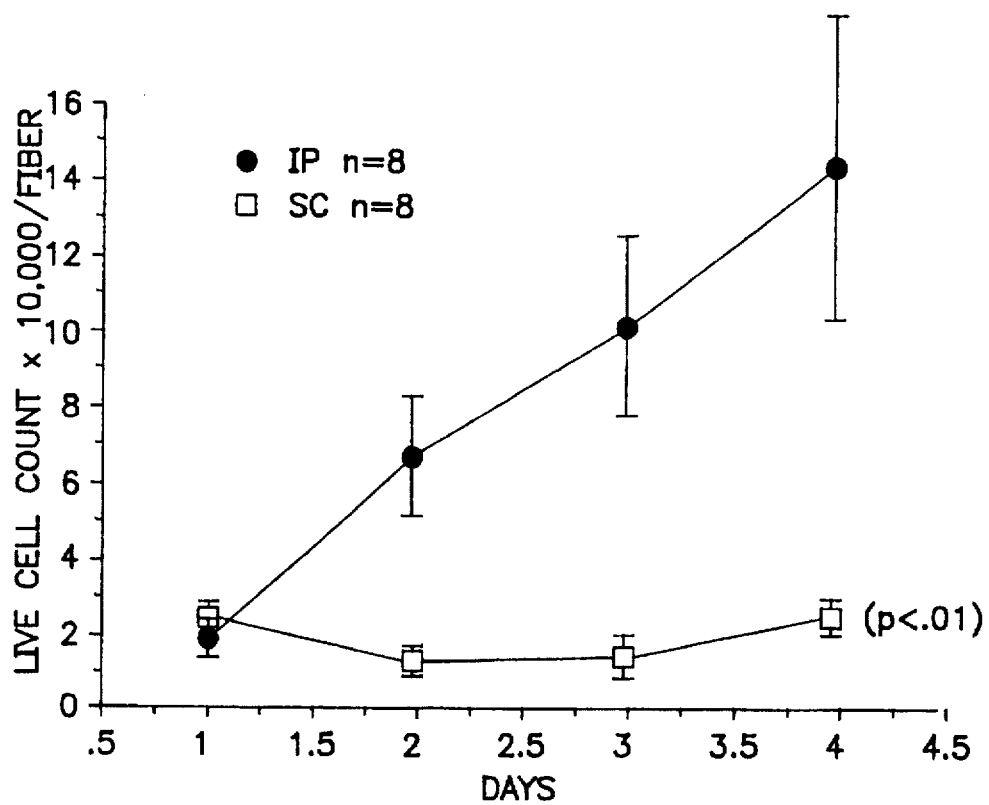
FIG. 4 is a graph of cell count versus time for intraperitoneal and subcutaneous implants.
Figure 5:
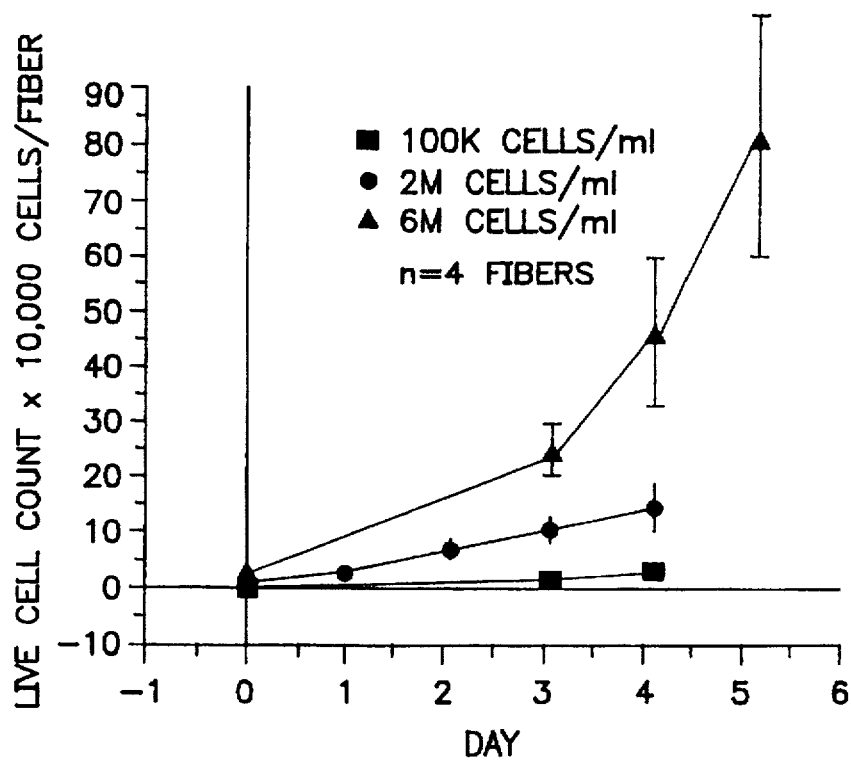
FIG. 5 is a graph of cell count versus time for different initial cell densities.

Tumor cells were sealed in semipermeable fiber segments and implanted both intraperitoneally and subcutaneously to compare the cell proliferations achieved at different implant locations (FIG. 4) and to evaluate the effect of different initial concentrations of cells (FIG. 5). The tumor cells employed were available under the designation MOLT-4 (Human T-Cell acute lymphoblastic leukemia ATCC CRL 1582) from Hyclone Industries maintained in RPM1-1640 with 10% fetal calf serum in a humidified incubator at 37 degrees centigrade and 5% carbon dioxide. The semipermeable hollow fiber membranes were 1.5 mm inner diameter, 30 mm long, polysulfone ultrafiltration fibers available from A. G. Technology, Needham, Mass. The mammals employed were Sprague-Dawley virus free rats from Charles River Laboratories, Wilmington, Mass. weighing 150–175 grams. Metophane inhalation anaesthesia was employed.

Different concentrations of cells suspension were prepared from cells in culture, as indicated in FIGS. 4 and 5. Thirty microliters of cell suspension were injected into the lumen of each polysulfone fiber. The ends of the fiber were sealed with resin by the technique described above. On day 0, fibers were implanted intraperitoneally in rats. On days 1, 2, 3, 4, 5, rats were sacrificed, and fibers from each rat were retrieved. Cell counts and percentage cell viability were determined for each fiber at the time of retrieval. Cell viability was determined by use of dye incorporation assay-Ethidium bromide and Acridine orange U.V. fluorescence staining. Hemocytometers and flow cytometers were used for cell counts.

Excellent viability (85%) of cells inside the fibers was documented by electron microscopy and by ethidium bromide U.V fluorescence staining. As can be seen from FIGS. 4 and 5, a linear growth curve over 72 hrs. was obtained using an initial cell density of 2 million cells/ml for fibers implanted intraperitoneally. Cell proliferation was 4 times greater intraperitoneally than subcutaneously ($p<0.01$). As can be seen from FIG. 5, an exponential curve resulted from a 6 million cells/ml initial concentration.

EXAMPLE 2

Figure 6:
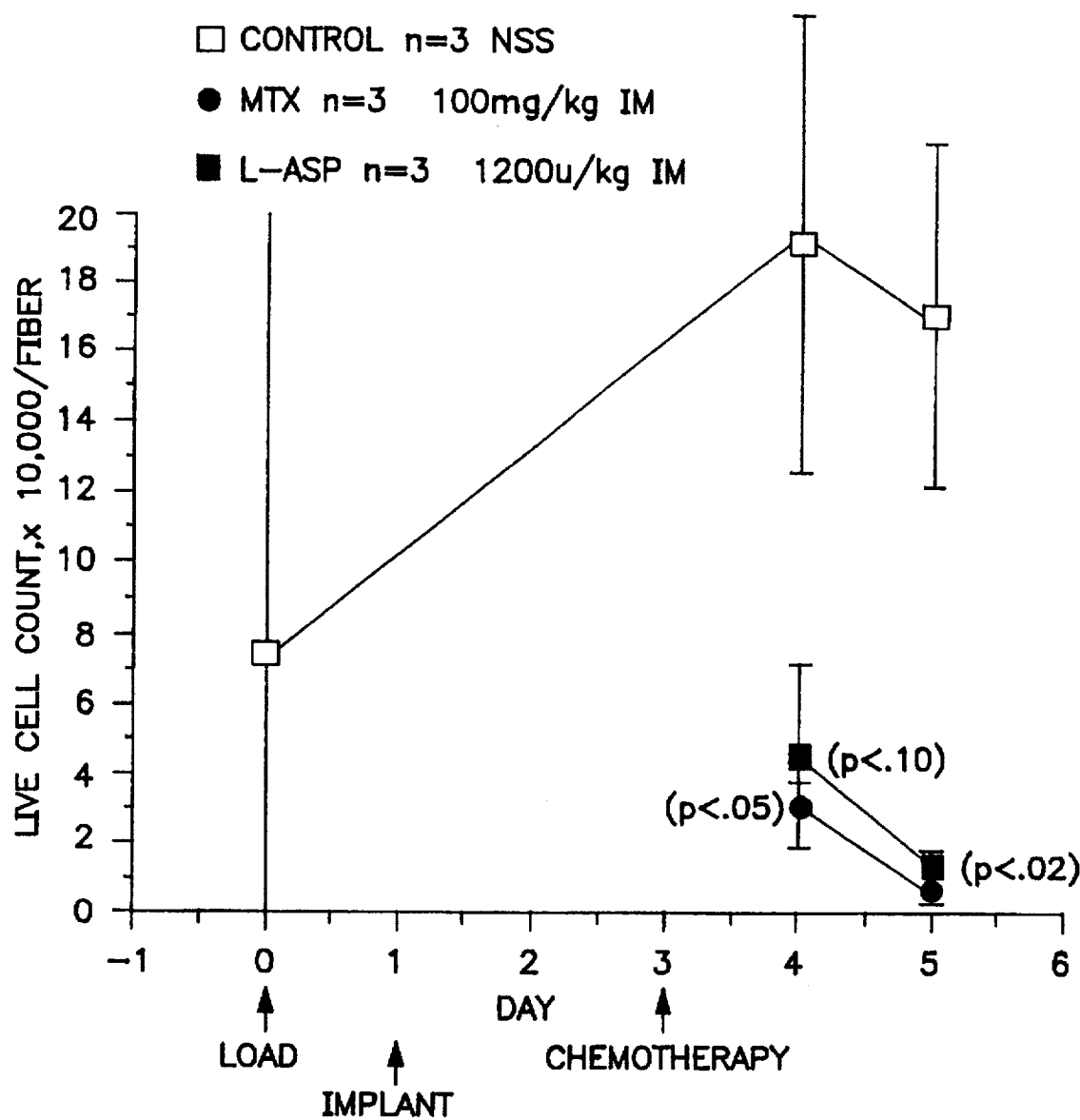
FIG. 6 is a graph of cell count versus time showing cytotoxic effect for two drugs administered 48 hours after implanting.

Rats were implanted with hollow fiber segments containing the MOLT-4 cell line as described above. Two chemotherapy agents were administered to two groups of rats, and a third group was used as a control. The fibers were implanted 24 hours after loading with cells, and chemotherapy agents were administered 48 hours after implanting. The rats in the two groups receiving treatment were treated with single drug therapy injected intramuscularly: methotrexate (MTX) 100 mg/kg and L-asparaginase (L-ASP) 1200 units/kg. The control rats received saline solution. Fibers were retrieved from each group of rats at 24 hours and 48 hours after chemotherapy and flushed with media. Cell counts were determined from single cell suspension. The results are shown on FIG. 6. No significant difference was observed when comparing cytotoxic effect at 24 hours versus 48 hours. A decreasing control cell number was noted after four days, implying that chemotherapy might be given earlier.

EXAMPLE 3

Figure 7:
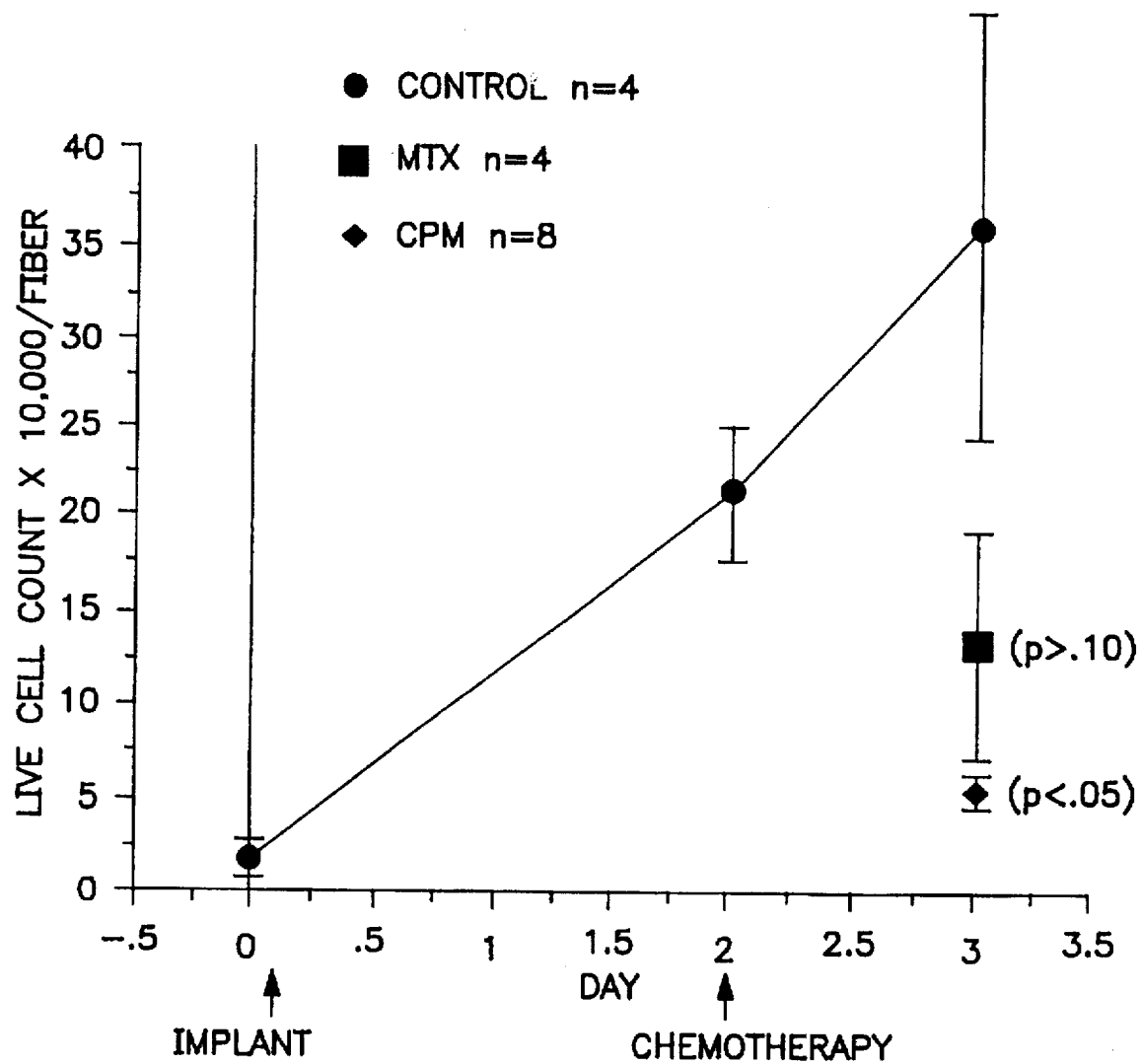
FIG. 7 is a graph of cell count versus time showing cytotoxic effect for two drugs administered 48 hours after implanting.

Rats were implanted with hollow fiber segments containing the MOLT-4 cell line as described above at a concentration of 2 million cells/ml; two chemotherapy agents were administered to two groups of rats, and a third group was used as a control. The fibers were implanted immediately after loading with cells, and chemotherapy agents were administered 48 hours after implanting. The rats in the two groups receiving treatment were treated with single drug therapy: methotrexate (MTX) 100 mg/kg injected intramuscularly, and cyclophosphamide (CPM) 100 mg/kg injected intravenously in the jugular vein. The control rats received saline solution. Fibers were retrieved from each group of rats 24 hours after chemotherapy and flushed with media. Cell counts were determined from single cell suspension. The results are shown on FIG. 7. This three-day assay shows cytotoxic effect of cyclophosphamide to be 85% inhibition and methotrexate to be 63% inhibition 24 hours post chemotherapy.

EXAMPLE 4

Figure 8:
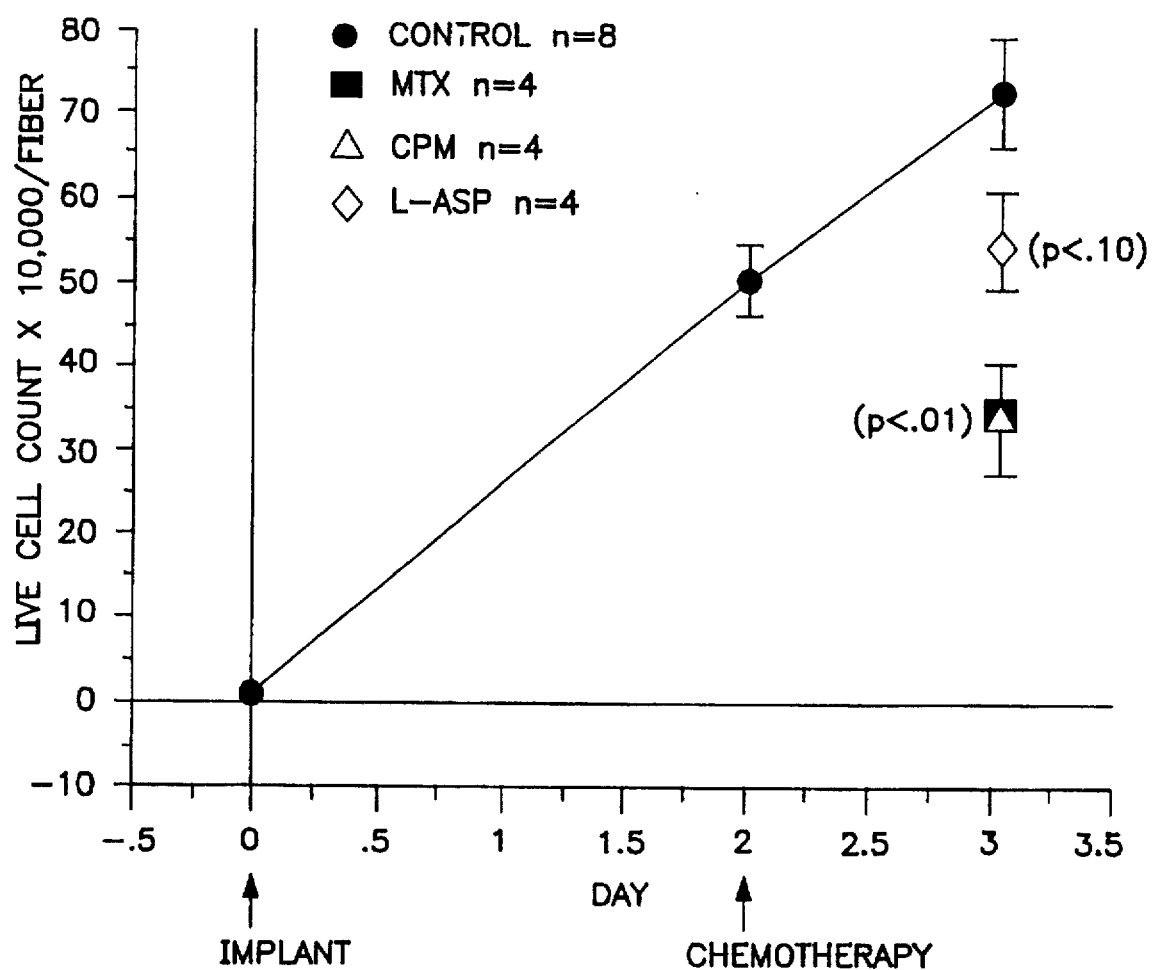
FIG. 8 is a graph of cell count versus time showing cytotoxic effect for three drugs administered 48 hours after implanting.

Rats were implanted with hollow fiber segments containing the MOLT-4 cell line as described above at a concentration of 2 million cells/ml; three chemotherapy agents were administered to three groups of rats, and a fourth group was used as a control. The fibers were implanted immediately after loading with cells, and chemotherapy agents were administered 48 hours after implanting. The rats in the three groups receiving treatment were treated with single drug therapy: methotrexate (MTX) 100 mg/kg injected intramuscularly, cyclophosphamide (CPM) 100 mg/kg injected intravenously, and L-asparaginase (L-ASP) 1200 units/kg injected intramuscularly. The control rats received saline solution. Fibers were retrieved from each group of rats 24 hours after chemotherapy and flushed with media. Cell counts were determined from single cell suspension. The results are shown on FIG. 8. This three-day assay shows cytotoxic effect of cyclophosphamide and methotrexate to be 53% inhibition and L-asparaginase to be 24% inhibition 24 hours post chemotherapy.

EXAMPLE 5

Figure 9:
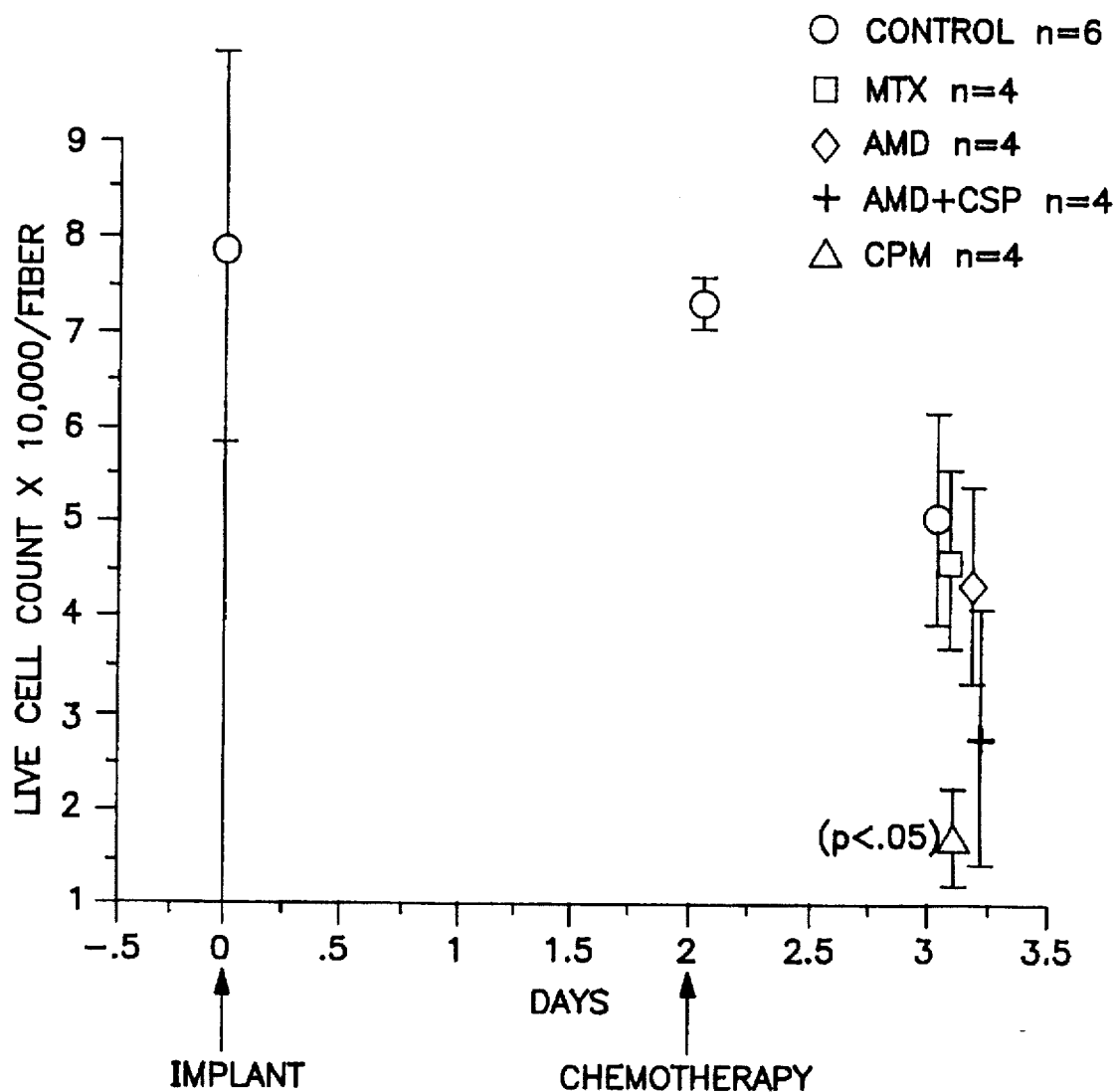
FIG. 9 is a graph of cell count versus time showing cytotoxic effect for four drug combinations administered 48 hours after implanting.

Lymphoblast cells were obtained from the blood of a human patient suffering from acute lymphoblastic leukemia in relapse, and a three-day assay according to the invention was performed to evaluate four potential treatments. The lymphoblasts were isolated by centrifugal separation employing the ISOLYMPH™ technique available in kit form from Gallard-Schlesinger Industries Inc., 584 Mineola Ave., Carle Place, N.Y. and described in a brochure entitled "One Step Method for Isolation of Pure Lymphocytes" from the same source. Rats were implanted with hollow fiber segments containing the lymphoblast cell suspension at a concentration of approximately 2 million cells/ml, and four chemotherapy agents were administered to four groups of rats, and a fifth group was used as a control. The fibers were implanted immediately after loading with cells, and chemotherapy agents were administered 48 hours after implanting. The rats in the three groups receiving treatment were treated with single drug therapy: methotrexate (MTX) 100 mg/kg injected intramuscularly, actinomycin-D (AMD) given intravenously, actinomycin-D (intravenously) and cyclosporine 100 mg/kg given orally (AMD+CSP), and cyclophosphamide (CPM) 100 mg/kg injected intravenously. The control rats received saline solution. Fibers were retrieved from each group of rats 24 hours after chemotherapy and flushed with media. Cell counts were determined from single cell suspension. The results are shown on FIG. 9. This three-day assay shows cytotoxic effect of cyclophosphamide to be 63% inhibition, combined actinomycin-D and cyclosporine to be 44% inhibition, and actinomycin-D alone to be 13% inhibition 24 hours post chemotherapy.

EXAMPLE 6

Lymphoblast cells were obtained from the bone marrow of a human patient suffering from acute lymphoblastic leukemia, and a three-day assay according to the invention was performed to evaluate a potential treatment. The bone marrow was removed from the spine using a needle, and lymphoblasts were isolated employing the same procedure as in Example 5. Rats were implanted with hollow fiber segments containing the lymphoblast cell suspension at a concentration of 2 million cells/ml, and methotrexate (MTX) 100 mg/kg was injected intramuscularly into one rat, and two other rats were used as a control. The fibers were implanted immediately after loading with cells, and the chemotherapy agent was administered 48 hours after implanting. The control rats received saline solution. Fibers were retrieved from the rats 24 hours after chemotherapy and flushed with media. Cell counts were determined from single cell suspension. In this case, fibers from the control and treated rat both had 92% viability of cells, indicating that the methotrexate was ineffective in inhibiting lymphoblasts.

In another patient, this one suffering from acute myelogenous leukemia, samples were taken from bone marrow as in Example 6, and a chemotherapy agent was administered, but bacterial contamination was discovered, rendering it impossible to obtain accurate test information.

We claim:

1. A method of determining the effectiveness of a cancer treatment comprising, providing elongated segments of semipermeable membrane hollow fibers having a pore size effective to permit passage of nutrients, and wherein said pore size excludes components of a mammal's immune system which induce tissue rejection, inserting tumor cells into said hollow fibers, sealing the ends of said hollow fibers, implanting said sealed hollow fibers intraperitoneally or subcutaneously into a non-human mammal, administering the cancer treatment, and monitoring the effectiveness of said treatment on the cells in said implanted hollow fibers.

2. The method of claim 1, wherein said mammal is immunocompetent.

3. The method of claim 2, wherein said mammal is a rat.

4. The method of claim 1, wherein said tumor cells are leukemic cells.

5. The method of claim 1, wherein said tumor cells are from a tumor of a patient.

6. The method of claim 5, wherein said cells are in suspension.

7. The method of claim 5, wherein said tumor cells are a tissue explant.

8. The method of claim 6, wherein said monitoring is the counting of viable cells in said fibers.

9. The method of claim 1, wherein said monitoring is a morphological examination of cells in said fibers.

10. The method of claim 1, wherein said implanting is intraperitoneally.

11. The method of claim 10, wherein said cancer therapy is a chemotherapeutic drug.

12. The method of claim 11, wherein said mammal is a rat.

13. The method of claim 1, wherein said implanting is subcutaneously.

14. The method of claim 13, wherein said cancer therapy is a chemotherapeutic drug.

15. The method of claim 14, wherein said mammal is a rat.

16. The method of claim 1, wherein said cancer treatment is a chemotherapeutic drug.

17. The method of claim 16, wherein said sealed fibers are implanted into a plurality of said mammals, and different chemotherapeutic drugs are administered to different of said plurality of mammals, and said monitoring is a comparison of results obtained from said different chemotherapeutic drugs.

18. The method of claim 1, wherein said cancer treatment is radiation therapy.

19. The method of claim 1, wherein different tumor cells are inserted into separate hollow fibers, and wherein said hollow fibers are sealed, implanted into said mammal, and the effectiveness of a cancer treatment on said different tumor cells is monitored.

20. The method of claim 1, wherein said fibers are polysulfone fibers.

21. The method of claim 20, wherein said fibers have pores with a molecular weight cutoff of 30,000 to 50,000 Daltons.

22. The method of claim 21, wherein said fibers have pores with a molecular weight cutoff of 30,000 Daltons.

23. The method of claim 1, wherein said pore size permits entry of immunotoxins.

* * * * *